United States Patent
Olek (10) Patent No.: US 11,643,687 B2
(45) Date of Patent: May 9, 2023

(54) LRP5 AS EPIGENETIC MARKER FOR THE IDENTIFICATION OF IMMUNE CELLS, IN PARTICULAR B-CELLS

(71) Applicant: Precision for Medicine GmbH, Berlin (DE)

(72) Inventor: Sven Olek, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 0 days.

(21) Appl. No.: 15/752,072

(22) PCT Filed: Sep. 22, 2016

(86) PCT No.: PCT/EP2016/072579
§ 371 (c)(1),
(2) Date: Feb. 12, 2018

(87) PCT Pub. No.: WO2017/050916
PCT Pub. Date: Mar. 30, 2017

(65) Prior Publication Data
US 2018/0216185 A1    Aug. 2, 2018

(30) Foreign Application Priority Data
Sep. 25, 2015 (GB) .................. 1516972

(51) Int. Cl.
*C12Q 1/6881* (2018.01)
(52) U.S. Cl.
CPC ..... *C12Q 1/6881* (2013.01); *C12Q 2600/154* (2013.01)
(58) Field of Classification Search
CPC .......... C12Q 1/6881; C12Q 2600/154
See application file for complete search history.

(56) References Cited

U.S. PATENT DOCUMENTS

2007/0269823 A1* 11/2007 Huehn ................. C12Q 1/6886
435/6.16
2013/0260378 A1* 10/2013 Olek ..................... C12Q 1/68
435/6.11

FOREIGN PATENT DOCUMENTS

| WO | 2013033627 A2 | 3/2013 | |
|----|----|----|----|
| WO | 2014170497 A2 | 10/2014 | |
| WO | WO-2014170497 A2 * | 10/2014 | ........... C12Q 1/6881 |
| WO | 2015181779 A2 | 12/2015 | |

OTHER PUBLICATIONS

May et al (Science (1988) vol. 241, p. 1441).*
Benner et al (Trends in Genetics (2001) vol. 17, pp. 414-418).*
Ehrlich et al. (2002 Oncogene vol. 21 p. 5400).*
Walsh et al (Genes & Development (1999) vol. 13, pp. 26-36).*
Brooks et al (Cancers Causes control (2009) vol. 20, pp. 1539-1550).*
Ushijima (Nature Reviews. 2005. 5: 223-231.*
Sabbioni et al (Mol Diagn 7(3):201-207 [2003].*
Zhang (PLOS Genetics (2009) vol. 5, e1000438).*
Kupers (Internationsl Journal of Epidemiology (2015) pp. 1224-1237).*
Zeilinger (PLOS one(2013) vol. 8, e63812, pp. 1-14).*
Alvarex-Garcia (arthritis & Rheumatology (2016) vol. 68, pp. 1876-1886).*
Cain (Journal of Bone and Mineral Research (2012) vol. 27, pp. 1451-1461).*
Bocker (Blood (2011) vol. 117, pp. e182-e189).*
Appay ( Journal of Immunology (2002) vol. 168, pp. 5954-5958).*
Harrison (Frontiers in Genetics (2011) vol. 2, article 74, pp. 1-13).*
Dahl (Biogerontology (2003) vol. 4, pp. 233-250).*
Farkas (Epigenomics (2014) vol. 6, pp. 179-191, published online May 9, 2014).*
Gloss (Cancer Letters vol. 342, Issue 2, Jan. 28, 2014, pp. 257-263).*
*Homo sapiens* low density lipoprotein receptor-related protein 5 (LRP5), RefSeqGene on chromosome 11 (GenBank accession NG_015835.1 (https://www.ncbi.nlm.nih.gov/nuccore/264681512?sat=21&satkey=51216775, Jun. 12, 2014).*
VanGuilder (BioTechniques vol. 44, Issue 5, Apr. 2008, pp. 619-626).*
Pabinger (Biomolecular Detection and Quantification (2014)vol. 1, pp. 23-33).*
Lo ( Journal of Molecular Diagnostics (2009) vol. 11, pp. 400-414).*
Küpers, L. K. et al., "DNA methylation mediates the effect of maternal smoking during pregnancy on birthweight of the offspring." Healthy Living: The European Congress of Epidemiology, Jun. 2015, 30: Abstract # 0 82, 753-754.
Vieweg, M. et al., "Methylation analysis of histone H4K12ac-associated promoters in sperm of healthy donors and subfertile patients." Clinical Epigenetics, 2015, 7 (31): 1-17.

* cited by examiner

*Primary Examiner* — Steven Pohnert (57) ABSTRACT

The present invention relates to a method, in particular an in vitro method, for identifying B cells, comprising analyzing the methylation status of at least one CpG position in the mammalian gene region for Low density lipoprotein receptor-related protein 5 (LRP5), wherein a demethylation or lack of methylation of said gene region is indicative for a B cell, when compared to a non-B cell. The analyses according to the invention can identify B cells on an epi-genetic level and distinguish them from all other cells in complex samples, such as, for example, other blood or immune cells. The present invention furthermore provides an improved method for quantifying B cells, in particular in complex samples. The method can be performed without a step of purifying and/or enriching cells, preferably in whole blood and/or non-trypsinized tissue. Further claimed are kits and specific primers and probes for identifying methylation.

18 Claims, 2 Drawing Sheets

Specification includes a Sequence Listing.

TpG-Specific PCR system

FIG. 2B

CpG-Specific PCR system

SEQUENCE LISTING

<160> NUMBER OF SEQ ID NOS: 11

<210> SEQ ID NO 1
<211> LENGTH: 488
<212> TYPE: DNA
<213> ORGANISM: Homo sapiens

<400> SEQUENCE: 1

```
gtatccaaat gtcctgccct ccaggtttca ttccttgccg taaaatatca cgttaaagga      60
aaatgttttg ttaaaagacc acagtcctgt cacctgagca cagtcgctgt tctcggttcc     120
tctgtggctt tccaggctgc aggtgcccat tggtattgcg gccgtgcgcc cggcgggcat     180
gaattagctg tgccgcctgg ctgctgacgg gacgcctcgc ctcgactgaa aactacctgg     240
agctgctcac ccaggggcaa cgtgaagaaa acgtgaaatt ctgtcgcttg ttgcagctga     300
cagcacggct gtgaggtccc agtgggcaga ggcctcgtgc agggcacctc accagccggg     360
atgtcagagc tggccagaag gagcggtgcc catggagggc tgccagtgcc cagagagcct     420
tccgaggtgt cacgttgggc agtgaaattc agagtcgggc agaggaggcc ctggggtcac     480
acagggat                                                             488
```

<210> SEQ ID NO 2
<211> LENGTH: 138
<212> TYPE: DNA
<213> ORGANISM: Homo sapiens

<400> SEQUENCE: 2

```
aatattacaa ccatacaccc aacaaacata aattaactat accacctaac tactaacaaa      60
acacctcacc tcaactaaaa actacctaaa actactcacc caaaaacaac ataaaaaaaa     120
cataaaattc tatcactt                                                  138
```

<210> SEQ ID NO 3
<211> LENGTH: 138
<212> TYPE: DNA
<213> ORGANISM: Homo sapiens

<400> SEQUENCE: 3

```
attaatatta cgaccgtacg cccgacgaac ataaattaac tataccgcct aactactaac      60
gaaacgcctc gcctcgacta aaaactacct aaaactactc acccaaaaac aacgtaaaaa     120
aaacgtaaaa ttctatcg                                                  138
```

<210> SEQ ID NO 4
<211> LENGTH: 22
<212> TYPE: DNA
<213> ORGANISM: Homo sapiens

<400> SEQUENCE: 4
atatccaaat atcctaccct cc                                           22

<210> SEQ ID NO 5
<211> LENGTH: 22
<212> TYPE: DNA
<213> ORGANISM: Homo sapiens

<400> SEQUENCE: 5
atttttgtgt gattttaggg tt                                           22

<210> SEQ ID NO 6
<211> LENGTH: 25
<212> TYPE: DNA
<213> ORGANISM: Homo sapiens

<400> SEQUENCE: 6
aatattacaa ccatacaccc aacaa                                        25

<210> SEQ ID NO 7
<211> LENGTH: 29
<212> TYPE: DNA
<213> ORGANISM: Homo sapiens

<400> SEQUENCE: 7
aagtgataga attttatgtt tttttttatg                                   29

<210> SEQ ID NO 8
<211> LENGTH: 27
<212> TYPE: DNA
<213> ORGANISM: Homo sapiens

<400> SEQUENCE: 8
ttagttgagg tgaggtgttt tgttagt                                      27

<210> SEQ ID NO 9
<211> LENGTH: 21
<212> TYPE: DNA
<213> ORGANISM: Homo sapiens

<400> SEQUENCE: 9
attaatatta cgaccgtacg c                                            21

<210> SEQ ID NO 10
<211> LENGTH: 25
<212> TYPE: DNA
<213> ORGANISM: Homo sapiens

<400> SEQUENCE: 10
cgatagaatt ttacgttttt tttac                                        25

<210> SEQ ID NO 11
<211> LENGTH: 18
<212> TYPE: DNA
<213> ORGANISM: Homo sapiens

<400> SEQUENCE: 11
acgaaacgcc tcgcctcg                                                18

LRP5 AS EPIGENETIC MARKER FOR THE IDENTIFICATION OF IMMUNE CELLS, IN PARTICULAR B-CELLS

CROSS REFERENCE TO RELATED APPLICATIONS

This application is a National Stage Application of International Application Number PCT/EP2016/072579, filed Sep. 22, 2016; which claims priority to Great Britain Patent Application No. 1516972.5, filed Sep. 25, 2015.

The Sequence Listing for this application is labeled "SeqList-12Feb18-ST25.txt", which was created on Feb. 12, 2018, and is 4 KB. The entire content is incorporated herein by reference in its entirety.

The present invention relates to a method, in particular an in vitro method, for identifying B cells, comprising analyzing the methylation status of at least one cytosine-phosphodiester-guanine (CpG) position in the mammalian gene region for Low density lipoprotein receptor-related protein 5 (LRP5), wherein a demethylation or lack of methylation of said gene region is indicative for a B cell, when compared to a non-B cell. The analyses according to the invention can identify B cells on an epigenetic level and distinguish them from all other cells in complex samples, such as, for example, other blood or immune cells. The present invention furthermore provides an improved method for quantifying B cells, in particular in complex samples. The method can be performed without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure B cells of the blood within any solid organs or tissue or any body fluid of a mammal.

BACKGROUND OF THE INVENTION

B cells or B lymphocytes are a type of lymphocyte in the humoral immunity of the adaptive immune system. B cells can be distinguished from other lymphocytes, such as T cells and natural killer cells (NK cells), by the presence of a protein on the B cell's outer surface known as a B cell receptor (BCR). This specialized receptor protein allows a B cell to bind to a specific antigen. In mammals, immature B cells are formed in the bone marrow.

The principal functions of B cells are to make antibodies in response to antigens, to perform the role of antigen-presenting cells (APCs), and to develop into memory B cells after activation by antigen interaction. B cells also release cytokines (proteins), which are used for signaling immune regulatory functions.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfate sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

WO 2012/162660 describes methods using DNA methylation arrays are provided for identifying a cell or mixture of cells and for quantification of alterations in distribution of cells in blood or in tissues, and for diagnosing, prognosing and treating disease conditions, particularly cancer. The methods use fresh and archival samples.

Dai et al. (in: Dai et al. Systematic CpG islands methylation profiling of genes in the wnt pathway in epithelial ovarian cancer identifies biomarkers of progression-free survival. Clin Cancer Res. 2011 Jun. 15; 17(12):4052-62. Epub 2011 Apr. 1.) disclose DNA methylation at promoter CpG islands (CGI) of Wnt pathway genes in ovarian tumors and identify biomarkers of patient progression-free survival (PFS). DNA methylation was associated with PFS in the LRP5 gene independent from clinical parameters (adjusted $P<0.05$). Increased methylation at the locus associated with increased hazard of disease progression. Nevertheless, only methylation at NKD1 and DVL1 was finally identified as independent predictors of PFS.

Accomando et al. (in: Accomando et al. Quantitative reconstruction of leukocyte subsets using DNA methylation. Genome Biol. 2014 Mar. 5; 15(3)) disclose that cell lineage-specific DNA methylation patterns distinguish normal human leukocyte subsets and can be used to detect and quantify these subsets in peripheral blood. They used DNA methylation to simultaneously quantify multiple leukocyte subsets and to identify cell lineage-specific DNA methylation signatures that distinguish human T cells, B cells, NK cells, monocytes, eosinophils, basophils and neutrophils. LRP5 is not mentioned.

In view of the above, it is an object of the present invention to provide an improved and in particular robust method based on DNA-methylation analysis as a superior tool in order to more conveniently and reliably detect, identify, discriminate, and quantify B cells.

The present invention solves the above object by providing method for identifying B cells in a sample, comprising analyzing the methylation status (bisulfite convertibility) of at least one CpG position in the mammalian (e.g. human) gene region for low density lipoprotein receptor-related protein 5 (LRP5), wherein preferably said gene region as analyzed is positioned based on/according to SEQ ID NO: 1, wherein a demethylation of said gene region is indicative for a B cell, when compared to a non-B cell.

The protein low density lipoprotein receptor-related protein 5 (LRP5, or BMND1, EVR1, EVR4, HBM, LR3, LRP7, OPPG, OPS, OPTA1, VBCH2) is a transmembrane low-density lipoprotein receptor that binds and internalizes ligands in the process of receptor-mediated endocytosis. This protein also acts as a co-receptor with Frizzled protein family members for transducing signals by Wnt proteins and was originally cloned on the basis of its association with diabetes mellitus type 1 in humans. The gene for human LRP5 is found on chromosome 11, 68,312,609-68,449,275 forward strand, Ensembl-ID: ENSG00000162337.

In the context of the present invention, the gene region shall comprise all of the genomic region relating to and encoding for LRP5. Thus, included are enhancer regions, promoter region(s), introns, exons, and non-coding regions (5'- and/or 3'-regions) that belong to LRP5. Preferred is thus a method according to the present invention, wherein the at least one CpG position is present in the 5' region upstream from the transcription start, promoter region, the 5' or 3' untranslated regions, exon, intron, exon/intron border and/or in the 3' region downstream of the transcriptional stop of the gene as analyzed.

The present invention is further based on the surprising identification of a region of the LRP5 gene by the inventors, as specific epigenetic marker, allowing the identification of B cells as well as the clinical routine application of said analysis.

In the context of the present invention, the genomic region of LRP5, in particular according to SEQ ID NO: 1 allows the identification of B cells. Surprisingly, the discriminatory pattern of bisulfite convertible and non-convertible cytosine is particularly and even exclusively limited to the genomic region according to SEQ ID NO: 1 for B cells as shown using the amplicon according to SEQ ID NO: 1, and in particular in the bisulfite converted sequences according to SEQ ID NOs: 2 and/or 3.

The inventors could demonstrate that in the B cells the CpG motifs as disclosed are almost completely demethylated (i.e. to more than 70%, preferably 80%, preferably, more than 90% and most preferred more than 95%), whereas the same motifs are completely methylated in all other immune cells.

The differential methylation of the CpG motifs within the aforementioned regions is a valuable tool to identify B cells, such as will be required/or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of B cells without purification or any staining procedures.

Another preferred aspect of the method according to the present invention then further comprises a quantification of the relative amount of B cells based on comparing relative amounts of said methylation frequency in the region as analyzed with relative amounts of the methylation frequency in a control gene, such as, for example, human glyceraldehyde 3-phosphate dehydrogenase (GAPDH). Said quantification is thus achieved based on the ratio of the bisulfite convertible DNA to non-convertible DNA in the genetic region of LRP5 (e.g. of SEQ ID NO: 1) as described and analyzed herein. Most preferred is a quantification of the relative amount of B cells is based on an (preferably parallel or simultaneous) analysis of the relative amount of bisulfite convertible DNA of cell-specific region for LRP5, and of the relative amount of bisulfite convertible DNA of cell-unspecific genes (preferably designated "control genes" or "control regions", such as, for example, the gene for GAPDH).

In a further preferred embodiment of the method according to the present invention, said analysis of bisulfite convertibility comprises amplification with at least one primer of suitable primer pairs that can be suitably designed based on SEQ ID NO: 1, preferably oligomers according to any of SEQ ID NOs: 2 to 4.

In contrast to FACS and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the context of methylation-specific PCR (MSP), HEAVYMETHYL™, SCORPION™, methylation-sensitive single-nucleotide primer extension (MS-SN-UPE), METHYLLIGHT™, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of the LRP5 gene region is produced that is a particularly preferred "tool" for performing the method(s) according to the present invention. Consequently, oligomers according to any of SEQ ID NOs: 4 and 5 or an amplicon as amplified by a primer pair based on SEQ ID NOs: 4 and 5 or 6 and 7 or 9 and 10 as mentioned herein constitute preferred embodiments of the present invention. Thus, the sequences of SEQ ID NOs: 1 to 3 (and, if needed, the complementary sequences thereto) can be used to design primers for amplifications, i.e. serve as "beacons" in the sequence as relevant. Similarly, additional primers and probes can be designed based on the amplicon according to SEQ ID NO: 1. Amplification can take place either in the genomic and/or bisulfite (i.e. "converted") DNA sequence.

Figure 1:
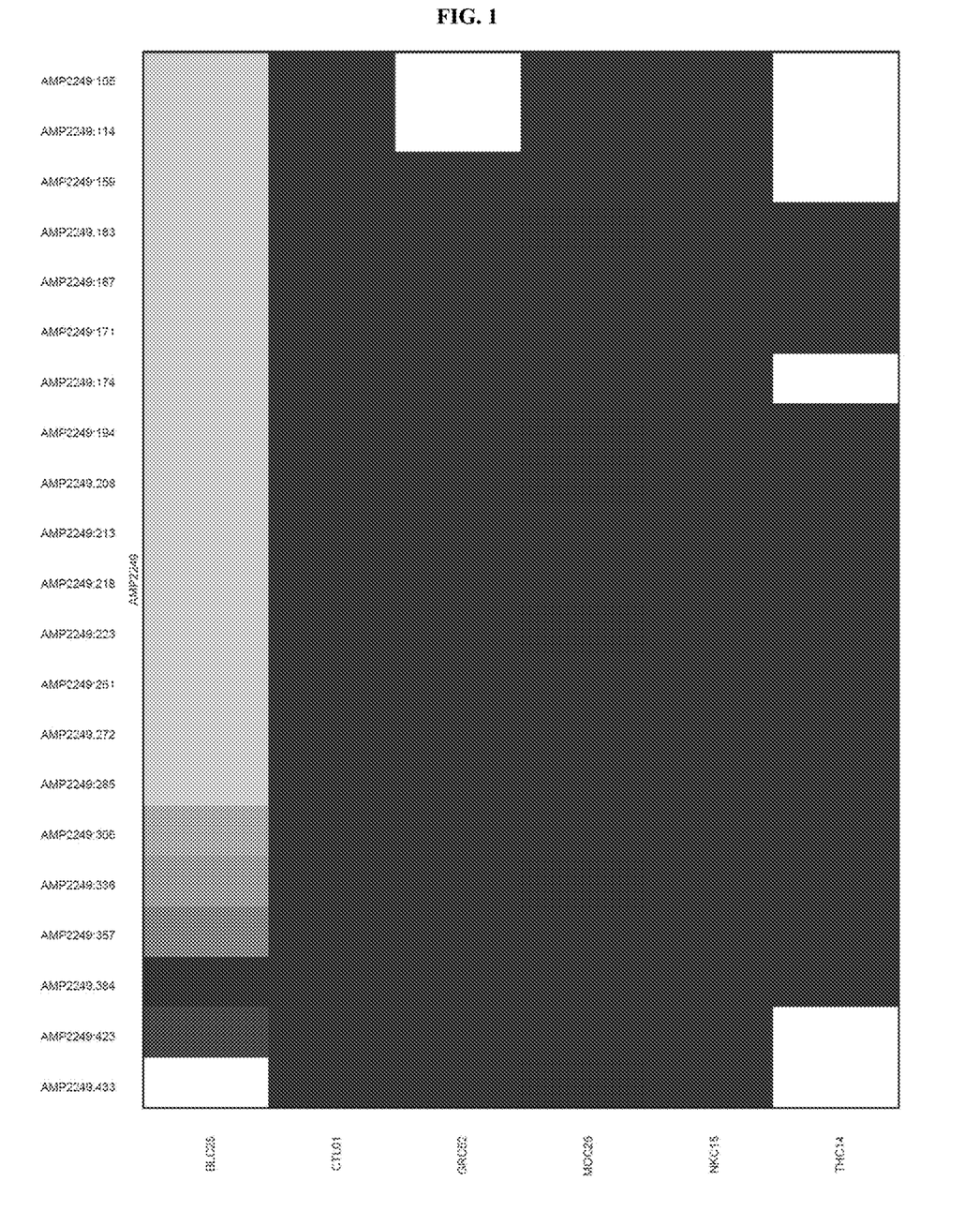
FIG. 1 shows the analysis of CpG sites on amplicon No. 2249 (SEQ ID NO: 1) according to the invention. The horizontal boxes in the table correspond to the CpG positions in the amplicon as analyzed (e.g. CpG 1, 2, etc.) with the positions indicated (105, 114, 159, 163, 167, 171, 174, 194, 208, 213, 218, 223, 261, 272, 285, 306, 336, 357, 384, 423, and 433, corresponding to CpG 3, 4, . . . etc.), and the columns correspond to the cell types as analyzed. The abbreviations at the bottom indicate BLC25=B-lymphocytes; CTL01=CD8$^+$ cytotoxic T-cells; GRC52=granulocytes; MOC26=CD14$^+$ monocytes; NKC15=CD56$^+$ NK-cells; and THC14=CD4$^+$ Helper T-cells, respectively.

The person of skill will furthermore be able to select specific subsets of CpG positions in order to minimize the amount of sites to be analyzed, for example at least one of CpG position selected from a CpG position in an amplicon according to SEQ ID NO: 1, and is preferably selected from CpG positions 3, 4, 5, 6, 7, 8, 9, 10, 11, 12, 13, 14, 15, 16, 17, 18, 19, 20, 21, 22, and 23 in the amplicon No. 2249 according to SEQ ID NO: 1. The positions are numerically counted from the 5'-end of an amplicon as generated and analyzed, and are designated as 105, 114, 159, 163, 167, 171, 174, 194, 208, 213, 218, 223, 261, 272, 285, 306, 336, 357, 384, 423, and 433 in FIG. 1. Preferred are combinations of 3, 4, 5, 6, 7, 8, 9, or 10 positions, the analysis of which produces sufficient data and/or information in order to be informative in the context of the present invention.

The person of skill will furthermore be able to select specific subsets of CpG positions in order to minimize the amount of sites to be analyzed, for example at least one of CpG position 5, 6, 7, 8, 9, 10, 11, 12, 13, 14, 15, 16, and/or 17 in the amplicon No. 2249 of the LRP5 specific bisulfite convertible region (SEQ ID NO: 1), or all sites as present on the bisulfite convertible region according to SEQ ID NO: 1.

In order to analyze the bisulfite convertibility of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, methylation-specific PCR (MSP), HEAVYMETHYL™, METHYLLIGHT™, methylation-sensitive single-nucleotide primer extension (MS-SNUPE), or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said B cells from all major peripheral blood cell types and/or non-blood cells, preferably, but not limited to, from follicular helper T cells, cytotoxic T-cells, granulocytes, monocytes, NK-cells, and T-helper cells, and other cell types derived from other organs than blood.

In yet another preferred embodiment of the method according to the present invention, the sample is selected from a mammalian body fluid, including human blood samples, or a tissue, organ or a sample of leukocytes or a purified or separated fraction of such tissue, organ or leukocytes or a cell type sample. Preferably, said mammal is a mouse, goat, dog, pig, cat, cow rat, monkey or human. The samples can be suitably pooled, if required.

Another preferred aspect of the method according to the present invention then further comprises the step of concluding on the immune status of said mammal based on said B cells. The B cells can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune activity status.

In yet another preferred embodiment of the methods according to the present invention, the mammal suffers from or is likely to suffer from autoimmune diseases, transplant rejections, infection diseases, cancer, and/or allergy as but not limited to Trypanosoma cruzi-infection, Malaria and HIV infection; Hematologic Malignancies as but not limited to chronic Myelogenous Leukemia, Multiple Myeloma, Non Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of B cells in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said B cells as e.g. a sample for cell transfer into a patient.

Another preferred aspect of the method according to the present invention then relates to a method as above, further comprising formulating said B cells as identified for transplantation into a patient. Pharmaceutical preparations for these purposes and methods for their production are performed according to methods known in the art of transplantation medicine.

Another preferred aspect of the method according to the present invention relates to an oligomer according to any of SEQ ID NOs: 4 to 11, or an amplicon according to SEQ ID NOs: 1 to 3.

Yet another preferred aspect of the present invention then relates to a kit for identifying, quantifying, and/or monitoring B cells in a mammal based on the analysis of the bisulfite accessibility of CpG positions in the gene region of LRP5, comprising components for performing a method according to invention as described herein, in particular a kit comprising a) a bisulfite reagent, and b) materials for the analysis of the methylation status of CpG positions selected from the CpG positions in the region according to SEQ ID NO: 1, such as an oligomer selected from the sequences according to SEQ ID NOs: 4 to 11.

The present invention also encompasses the use of oligomers or amplicon or a kit according to the present invention for identifying and/or for monitoring B cells in a mammal as described herein.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxycytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ratio=$a/b$ $a=\Sigma$(C and/or mC and/or hmC and/or fC and/or cC)
$b=\Sigma$(C and/or mC and/or hmC and/or fC and/or cC),
whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

In summary, using the LRP5 genetic region and in particular the amplicon as described herein as a marker, the inventors very specifically identified, quantified and particularly differentiated B cells, and in their relation to other cell types in a sample, for example to other blood cells.

The invention will now be further described based on the following examples and with reference to the accompanying figures and the sequence listing, without being limited thereto. For the purposes of the present invention, all references as cited herein are incorporated by reference in their entireties.

SEQ ID NO: 1 shows the genomic sequence of amplicon AMP2249 according to the present invention.

SEQ ID NOs: 2 and 3 show the sequences of bisulfate-converted target-regions of preferred qPCR-assay-systems of the invention.

SEQ ID NOs: 4 to 11 show the sequences of specific oligomers (primers and probes) according to the present invention.

EXAMPLES

Example 1

In order to identify B-cells, qPCR was performed on bisulphite converted samples stemming from the human genomic region according to the following sequence (AMP2249, SEQ ID NO: 1), relevant CpGs are shaded in gray:

```
GTATCCAAATGTCCTGCCCTCCAGGTTTCATTCCTTGCCGTAAAATATCACGTTAAAGGAAAATGTTTTGTTAAA

AGACCACAGTCCTGTCACCTGAGCACAGTCGCTGTTCTCGGTTCCTCTGTGGCTTTCCAGGCTGCAGGTGCCCAT
```

```
TGGTATTGCGGCCGTGCGCCCGGCGGGCATGAATTAGCTGTGCCGCCTGGCTGCTGACGGGACGCCTCGCCTCGA

CTGAAAACTACCTGGAGCTGCTCACCCAGGGGCAACGTGAAGAAAACGTGAAATTCTGTCGCTTGTTGCAGCTGA

CAGCACGGCTGTGAGGTCCCAGTGGGCAGAGGCCTCGTGCAGGGCACCTCACCAGCCGGGATGTCAGAGCTGGCC

AGAAGGAGCGGTGCCCATGGAGGGCTGCCAGTGCCCAGAGAGCCTTCCGAGGTGTCACGTTGGGCAGTGAAATTC

AGAGTCGGGCAGAGGAGGCCCTGGGGTCACACAGGGAT
```

For the actual epigenetic profiling of the amplicon region in blood cell subtypes, the immune cell populations as analyzed were as follows (see FIG. 1)
BLC25=B-lymphocytes
CTL01=CD8+ cytotoxic T-cells
GRC52=granulocytes
MOC26=CD14+ monocytes
NKC15=CD56+ NK-cells
THC14=CD4+ Helper T-cells The bisulfate-converted target-regions of preferred qPCR-assay-system as developed were:

```
TpG-specific (SEQ ID No. 2):
ATATCCAAATATCCTACCCTCCAAATTTCATTCCTTACCATAAAATATCACATTAAAAAAAAATATTTTATTAAA

AAACCACAATCCTATCACCTAAACACAATCACTATTCTCAATTCCTCTATAACTTTCCAAACTACAAATACCCAT

TAATATTACAACCATACACCCAACAAACATAAATTAACTATACCACCTAACTACTAACAAAACACCTCACCTCAA

CTAAAAACTACCTAAAACTACTCACCCAAAAACAACATAAAAAAAACATAAAATTCTATCACTTATTACAACTAA

CAACACAACTATAAAATCCCAATAAACAAAAACCTCATACAAAACACCTCACCAACCAAAATATCAAAACTAACC

AAAAAAAACAATACCCATAAAAAACTACCAATACCCAAAAAACCTTCCAAAATATCACATTAAACAATAAAATTC

AAAATCAAACAAAAAAAACCCTAAAATCACACAAAAT

CpG-specific: (SEQ ID No. 3):
ATATCCAAATATCCTACCCTCCAAATTTCATTCCTTACCGTAAAATATCACGTTAAAAAAAAATATTTTATTAAA

AAACCACAATCCTATCACCTAAACACAATCGCTATTCTCGATTCCTCTATAACTTTCCAAACTACAAATACCCAT

TAATATTACGACCGGTACGCCCGACGAACATAAATTAACTATACCGCCTACTAACTAACGAAACGCCTCGCCTCGA

CTAAAAACTACCTAAAACTACTCACCCAAAAACAACGTAAAAAAAACGTAAAATTCTATCGCTTATTACAACTAA

CAACACGACTATAAAATCCCAATAAACAAAAACCTCGTACAAAACACCTCACCAACCGAAATATCAAAACTAACC

AAAAAAACGATACCCATAAAAAACTACCAATACCCAAAAAACCTTCCGAAATATCACGTTAAACAATAAAATTC

AAAATCGAACAAAAAAAACCCTAAAATCACACAAAAT
```

The respective sequence of the assay-target region is underlined.

The following primers and probe were used for the qPCR:

| Forward amplification primer | 2249r | ATATCCAAATATCCTACCCTCC (SEQ ID No. 4) |
|---|---|---|
| Reverse amplification primer | 2249q | ATTTTTGTGTGATTTTAGGGTT (SEQ ID No.5) |
| Forward primer TpG-specific | 2249r_T_fw | AATATTACAACCATACACCCAACAA (SEQ ID No. 6) |
| Reverse primer TpG-specific | 2249q_T_rev | AAGTGATAGAATTTTATGTTTTTTTTATG (SEQ ID No. 7) |
| Probe TpG-specific | 2249_TP | TTAGTTGAGGTGAGGTGTTTTGTTAGT (SEQ ID No. 8) |
| Forward primer CpG-specific | 2249r_C_fw | ATTAATATTACGACCGTACGC (SEQ ID No. 9) |
| Reverse primer CpG-specific | 2249q_C_rev | CGATAGAATTTTACGTTTTTTTAC (SEQ ID No. 10) |

-continued

| Probe CpG-specific | 2249_CP | ACGAAACGCCTCGCCTCGA (SEQ ID No. 11) |

Figure 2A:
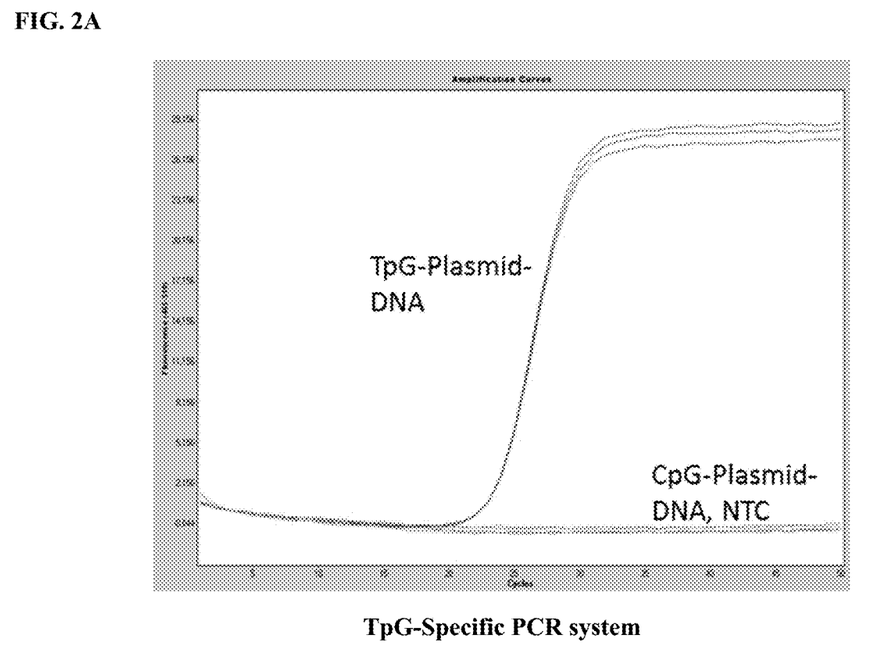
FIGS. 2A-2B are series of graphs depicting the specificity of the TpG-specific PCR-system using plasmid-DNA test-template (FIG. 2A) and the specificity of the CpG-specific PCR-system using plasmid-DNA test-template (FIG. 2B).
Figure 2B:
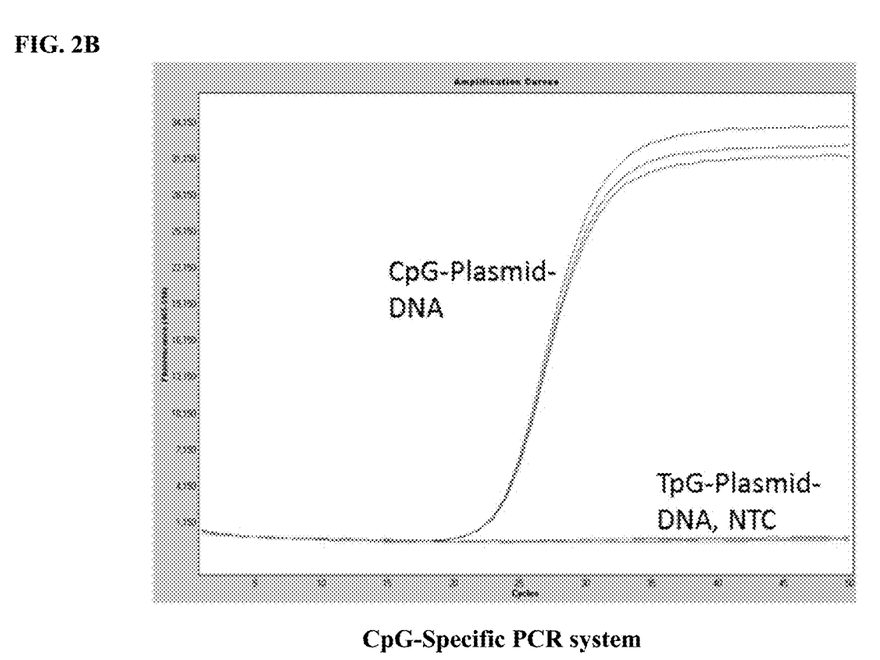

The specificity of the TpG-specific PCR-system was demonstrated using test-templates (plasmid-DNA) as shown in FIGS. 2A-2B.

The cell type specificity (as measured by qPCR) was found as follows:

| Immune cell population | CP-value TpG-PCR | TpG-copies | CP-value CpG-PCR | CpG-copies | B-cells [%] |
|---|---|---|---|---|---|
| CD8+ cells | 35.3 | 11.9 | 26.3 | 5323.3 | 0.22 |
| CD4+ cells | 34.1 | 17.9 | 26.4 | 4900.0 | 0.36 |
| B-cells | 25.1 | 8213.3 | 31.7 | 128.0 | 98.47 |
| Granulocytes | 35.0 | 13.1 | 26.1 | 5980.0 | 0.22 |
| Monocytes | 33.9 | 19.6 | 25.9 | 6913.3 | 0.28 |
| GRK01 | 31.4 | 94 | 26.8 | 3723.3 | 2.46 |

The invention claimed is:

1. A method of producing and detecting an amplicon from a bisulfite treated human low density lipoprotein receptor-related protein 5 (LRP5) gene, the method comprising:
   (a) bisulfite treating human genomic DNA from a human sample containing B cells to convert unmethylated cytosines to uracils;
   (b) producing the amplicon by amplifying a region of the human LRP5 gene from the bisulfite treated DNA using quantitative polymerase chain reaction (qPCR), wherein the qPCR is performed with methylation specific primers; and
   (c) detecting the amplicon with a probe comprising the nucleic acid sequence of SEQ ID NO: 8;
   wherein the region of the human LRP5 gene comprises a nucleotide sequence comprising SEQ ID NO: 1 prior to bisulfite treatment and a bisulfite convertible cytosine at at least one of cytosine-phosphodiester-guanine (CpG) positions 159, 163, 167, 171, 174, 194, 208, 213, 218, 223, 261, 272, and 285 relative to SEQ ID NO: 1.

2. The method according to claim 1, wherein the human LRP5 gene is from a sample comprising blood, a tissue, an organ, or cells.

3. The method according to claim 1, further comprising, after producing the amplicon, distinguishing B cells from at least one of the human immune cell types selected from follicular helper T cells, cytotoxic T-cells, granulocytes, monocytes, natural killer (NK) cells, and T-helper cells.

4. The method according to claim 1, wherein said method is performed without a step of purifying and/or enriching cells from the sample.

5. The method of claim 1 performed using a kit comprising a) a bisulfite reagent, and b) materials for detecting the bisulfite convertible cytosine at the at least one CpG positions.

6. The method according to claim 1, wherein the amplifying comprises using an oligomer comprising a nucleic acid sequence of any of SEQ ID NOs: 4 to 11.

7. The method according to claim 1, wherein at least four of the CpG positions selected from CpG positions 159, 163, 167, 171, 174, 194, 208, 213, 218, 223, 261, 272, and 285 relative to SEQ ID NO: 1 comprise bisulfite convertible cytosine.

8. The method according to claim 4, wherein the sample is whole blood and/or non-trypsinized tissue.

9. The method according to claim 1, wherein the human LRP5 gene is from a blood sample.

10. The method according to claim 1, further comprising
    (d) detecting methylation status of the at least one CpG position from the amplicon.

11. A method of producing and detecting an amplicon, the method comprising:
    a) bisulfite treating DNA from a human sample containing B cells to generate bisulfite treated DNA where unmethylated cytosines are converted to uracils,
    b) producing the amplicon with quantitative polymerase chain reaction (qPCR), and
    c) detecting the amplicon with a probe comprising the nucleic acid sequence of SEQ ID NO: 8,
    wherein the amplicon comprises SEQ ID NO: 2.

12. The method of claim 11, wherein the qPCR uses oligomers of any one of SEQ ID NOs: 4-7.

13. The method of claim 11, wherein the sample is a blood sample.

14. The method of claim 11, further comprising
    d) detecting methylation status of at least one cytosine-phosphate-guanine (CpG) position in SEQ ID NO: 1 from the amplicon.

15. The method of claim 1, wherein the amplicon comprises cytosine-adenine (CA) at at least one of the CpG positions 159, 163, 167, 171, 174, 194, 208, 213, 218, 223, 261, 272, and 285 relative to SEQ ID NO: 1.

16. A method of producing and detecting an amplicon, the method comprising:
    a) bisulfite treating DNA from a human sample containing B cells to generate bisulfite treated DNA where unmethylated cytosines are converted to uracils,
    b) producing the amplicon with quantitative polymerase chain reaction (qPCR), and
    c) detecting the amplicon with a probe comprising the nucleic acid sequence of SEQ ID NO: 8,
    wherein the amplicon comprises nucleotides 203-228 of SEQ ID NO: 2 and cytosine-adenine (CA) at CA positions 208, 213, 218, and 223 relative to SEQ ID NO: 2.

17. The method of claim 16, wherein the amplicon comprises nucleotides 152-289 of SEQ ID NO: 2.

18. The method of claim 17, wherein the amplicon comprises cytosine-adenine (CA) at positions 167, 171, 174, 194, 208, 213, 218, and 223 relative to SEQ ID NO: 2.

* * * * *